US00PP16179P3

(12) United States Plant Patent
Zaiger et al.

(10) Patent No.: US PP16,179 P3
(45) Date of Patent: Jan. 3, 2006

(54) PEACH TREE

(50) Latin Name: *Prunus persica*
Varietal Denomination: Sauzee Queen

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 186 days.

(21) Appl. No.: 10/843,154

(22) Filed: May 12, 2004

(65) Prior Publication Data

US 2005/0257302 P1 Nov. 17, 2005

(51) Int. Cl.
*A01H 5/00* (2006.01)

(52) U.S. Cl. ..... Plt./197
(58) Field of Classification Search ..... Plt./197
See application file for complete search history.

*Primary Examiner*—Anne Marie Grunberg
*Assistant Examiner*—Annette H Para

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying irrigation and fertilization. Its novelty consist of the following combination of desirable features:

1. Fruit with an attractive orange-red skin color.
2. Producing fruit ripening in the early maturity season.
3. Producing peento shaped fruit (saucer, donut or flat shape).
4. Fruit with firm, white flesh, good flavor and eating quality.
5. Having a moderate winter chilling requirement of approximately 500 hours.
6. Vigorous, upright growth habit.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peaches and nectarines, which are known to us, and mentioned herein, 'Carolyn' Peach (non-patented), 'Fayette' Peach (non-patented), 'May Crest' Peach (U.S. Plant Pat. No. 4,064), 'Saturn' Peach (U.S. Plant Pat. No. 5,123), and 'May Grand' Nectarine (U.S. Plant Pat. No. 2,794).

ORIGIN OF THE VARIETY

The new and distinct peach tree (*Prunus persica*) was originated by us in our experimental orchard located near Modesto, Calif., as seed from an open pollinated proprietary seedling with field identification number 333LH428. The (333LH428) seedling originated from a cross between two proprietary seedlings with field identification numbers 72LD525 and 294LF27. The maternal parent (72LD525) originated from crosses between 'Carolyn' Peach (non-patented), 'Fayette' Peach (non-patented) and 'May Grand' Nectarine (U.S. Plant Pat. No. 2,794). The paternal parent was a peento peach of unknown parentage. A large group of these open pollinated seedlings were planted and maintained on their own root system, during which time we recognized the desirable peento fruit characteristic, (commonly referred to as saucer or donut shape), of the present new, early maturing variety and selected it for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a productive bearer of medium size, firm, white flesh, clingstone fruit. The fruit is further characterized by being early in maturity, with an attractive orange-red blush, having a mild, sweet, sub-acid flavor with very good eating quality. The tree has a moderate winter chilling requirement of approximately 500 hours, is hardy in all stone fruit growing areas of California and in comparison to the early maturing 'May Crest' Peach (U.S. Plant Pat. No. 4,064), the fruit of the new variety is white fleshed compared to yellow, is peento shape compared to globose, is sub-acid compared to acidic and matures in the same early maturity season. In comparison to its immediate seed parent (333LH428), the fruit of the new variety is larger in size, matures approximately 60 days earlier and has the same peento shape.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, pruned to 3 to 3.5 meters in height for economical harvesting of fruit.

*Vigor.*—Vigorous, growth of 1.5 to 2 meters the first growing season. Varies with soil type, fertility and cultural practices.

*Form.*—Upright, usually pruned to vase shape.

*Branching habit.*—Upright, crotch angle approximately 35°, increases with heavy crop load.

*Productivity.*—Productive, thinning and spacing necessary for desired marketable size fruit. Number of fruit set varies with climatic conditions during blooming period.

*Bearer.*—Regular, has had 3 consecutive years of good production. No alternate bearing observed.

*Fertility.*—Self fertile.

*Density.*—Medium dense.

*Hardiness.*—Hardy in all stone fruit growing areas of California. Winter chilling requirement approximately 500 hours at or below 45° F.

Trunk:

*Size.*—Medium. Average circumference 41.6 cm at 28.6 cm above ground on a 5 year old tree.

*Stocky.*—Medium.

*Texture.*—Medium shaggy, becomes rougher with age.

*Color.*—Varies from 10YR 6/2 to 10YR 5/2.

Branches:

*Size.*—Medium. Average circumference 19.3 cm at 1.5 meters above ground.

*Surface texture.*—New growth smooth. Mature growth medium rough.

*Lenticels.*—Large size. Average number of 27 in a 25.8 square cm section. Average length 4.3 mm. Average width 1.5 mm. Color varies from 7.5YR 6/6 to 7.5YR 5/8.

*Color.*—New growth varies from 2.5GY 5/6 to 5GY 5/8. Mature growth varies from 5YR 3/6 to 2.5YR 4/4.

Leaves:

*Size.*—Very large. Average length 185.6 mm. Average width 48.1 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentation over midrib and leaf veins. Lower surface relatively smooth, small ridges created by midrib and pinnate venation. Both surfaces glabrous.

*Petiole.*—Medium to large size. Average length 11.7 mm. Average width 1.9 mm. Longitudinally grooved. Surface glabrous. Color varies from 5GY 8/4 to 5GY 7/8.

*Glands.*—Reniform. Size — medium to large. Average length 1.5 mm. Average width 0.5 mm. Average number 3, varies from 2 to 4. Located on base of leaf blade and upper portion of petiole. Color varies from 5GY 7/6 to 5GY 7/8.

*Color.*—Upper surface varies from 5GY 4/6 to 5GY 3/6. Lower surface varies from 5GY 5/4 to 5GY 4/4. Midvein color varies from 5GY 8/4 to 5GY 7/6.

Flower buds:

*Size.*—Large. Average length 19.7 mm. Average width 11.4 mm.

*Hardiness.*—Hardy in all stone fruit growing areas of California.

*Form.*—Conical, becoming elongated before opening.

*Pedicel.*—Medium. Average length 4.2 mm. Average width 1.1 mm. Color varies from 2.5GY 6/10 to 5GY 6/8.

*Color.*—Varies from 7.5RP 5/2 to 5RP 7/8.

Flowers:

*Size.*—Large. Average height 20.6 mm. Average diameter 38.4 mm.

*Petals.*—Number 5, alternately arranged to sepals. Shape varies from orbicular to elongated. Average length 22.6 mm. Average width 19.0 mm. Margin — sinuate. Color vaires from 5RP 7/8 to 5RP 8/6.

*Sepals.*—Number 5, alternately arranged to petals. Shape — triangular. Upper surface glabrous, lower surface pubescent. Size — large. Average length 6.4 mm. Average width 4.8 mm. Color — upper surface varies from 5GY 5/6 to 5GY 4/6. Lower surface varies from 10R 4/2 to 10R 3/4.

*Stamens.*—Average number per flower 41, varies from 38 to 42. Average filament length 16.9. mm. Filament color varies from N 9.5/ to 5RP 9/2. Anther color varies from 7.5R 4/10 to 5R 3/10.

*Pollen.*—Self fertile. Color varies from 2.5Y 8.5/12 to 5Y 8/10.

*Pistil.*—Normally one. Surface — pubescent. Average length 14.4 mm. Stigma height average 1.7 mm below anthers.

*Fragrance.*—Slight.

*Blooming period.*—Date of first bloom Feb. 27, 2003. Date of petal fall Mar. 8, 2003. Varies slightly with climatic conditions.

*Pedicel.*—Size — medium. Average length 4.4 mm. Average width 1.3 mm. Color varies from 5GY 6/8 to 5GY 5/8.

*Number flowers per flower bud.*—Usually one.

*Color.*—Varies from 5RP 8/6 to 5RP 7/12.

Fruit:

*Maturity when described.*—Firm ripe.

*Date of first picking.*—May 21, 2003.

*Date of last picking.*—May 26, 2003, varies slightly with climatic conditions.

*Size.*—Medium. Average diameter axially 36.9 mm. Average transversely in suture plane 63.3 mm. Average weight 96.6 grams. Average weight varies slightly with fertility of the soil, amount of thinning and climatic conditions.

*Form.*—Peento shape.

*Suture.*—Shallow, extends from base to apex.

*Ventral surface.*—Nearly smooth, slightly lipped.

*Apex.*—Retuse.

*Base.*—Retuse.

*Cavity.*—Rounded to slightly elongated in suture plane. Average depth 2.0 mm. Average diameter 13.5 mm.

Stem:

*Size.*—Small. Average length 5.1 mm. Average diameter 4.1 mm.

*Color.*—Varies from 5GY 6/8 to 5GY 6/10.

Flesh:

*Ripens.*—Relatively even, slightly delayed near the stone.

*Texture.*—Firm, meaty.

*Fibers.*—Few, small, tender.

*Firmness.*—Firm, much firmer than the peento fruit of 'Saturn' Peach (U.S. Plant Pat. No. 5,123).

*Aroma.*—Moderate.

*Amydgalin.*—Undetected.

*Eating quality.*—Very good.

*Flavor.*—Very good.

*Juice.*—Moderate, enhances flavor.

*Brix.*—Average 9.8°, varies slightly with amount of fruit per tree and climatic conditions.

*Color.*—Varies from 7Y 9/2 to 10Y 9/2. Pit cavity varies from 7.5Y 8.5/4 to 5Y 8.5/4.

Skin:

*Thickness.*—Medium.

*Surface.*—Smooth.

*Down.*—Moderate amount, short in length.

*Tendency to crack.*—Very slight.

*Color.*—Ground color varies from 7.5Y 8/4 to 10Y 8.5/4. Overspread with 5R 4/10 to 7.5R 4/8 on approximately 60% of surface.

*Tenacity.*—Tenacious to flesh.

*Astringency.*—None.

Stone:

*Type.*—Clingstone.

*Size.*—Medium. Average length 13.7 mm. Average width 22.4 mm. Average thickness 14.2 mm.

*Form.*—Peento shape, resembling shape of fruit.

*Base.*—Straight, nearly flat.

*Apex.*—Flat.

*Surface.*—Irregularly furrowed toward apex, pitted toward base. Pits vary from round to elongated.

*Sides.*—Relatively equal.

*Ridges.*—Relatively narrow and sharp.

*Tendency to split.*—None.

*Color.*—Varies from 7.5YR 7/6 to 7.5YR 6/8.

Kernal:

*Form.*—Ovate.

*Taste.*—Bitter.

*Viability.*—Poor, incomplete embryo.

*Size.*—Medium. Average length 10.6 mm. Average width 9.5 mm. Average depth 5.9 mm.

*Skin.*—Color varies from 5YR 4/6 to 5YR 4/8 when fresh.

Use: Dessert. Market — local and long distance.

Keeping quality: Good, held firm in cold storage 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance of susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peento peach tree, substantially as illustrated and described, characterized by its large size, vigorous, upright growth and being a productive bearer of medium size, firm, white flesh, peento fruit with very good flavor and eating quality; the tree is further characterized by having a moderate winter chilling requirement of approximately 500 hours at or below 45° F., being hardy in all stone fruit growing areas of California with fruit ripening in the early maturing season.

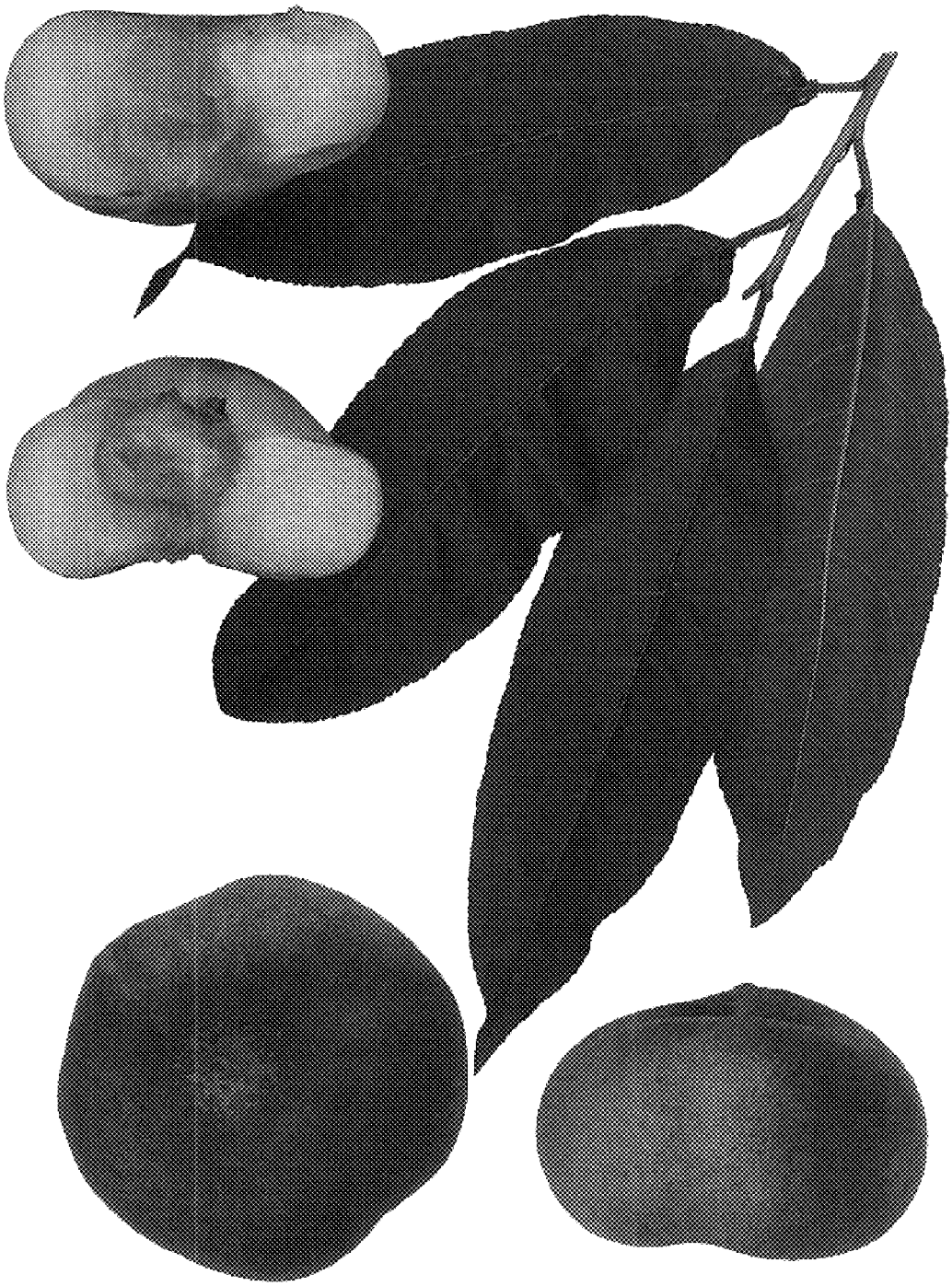

* * * * *